United States Patent [19]
Wallajapet et al.

[11] Patent Number: 5,948,829
[45] Date of Patent: Sep. 7, 1999

[54] PROCESS FOR PREPARING AN ABSORBENT FOAM

[75] Inventors: Palani Raj Ramaswami Wallajapet, Wauwatosa; Jian Qin, Appleton; Gary D. Williams, Neenah, all of Wis.

[73] Assignee: Kimberly-Clark Worldwide, Inc., Neenah, Wis.

[21] Appl. No.: 08/978,263

[22] Filed: Nov. 25, 1997

[51] Int. Cl.⁶ .................................................. C08J 9/28
[52] U.S. Cl. ........................... 521/64; 521/84.1; 521/141; 521/149; 521/182; 536/20
[58] Field of Search ........................... 521/64, 84.1, 141, 521/149, 182; 536/20

[56] References Cited

U.S. PATENT DOCUMENTS

| | | | |
|---|---|---|---|
| 3,705,585 | 12/1972 | Saffro | 128/303.1 |
| 3,763,857 | 10/1973 | Schrading | 128/132 D |
| 3,812,856 | 5/1974 | Duncan et al. | 128/285 |
| 3,815,601 | 6/1974 | Schaefer | 128/285 |
| 3,888,248 | 6/1975 | Moore et al. | 128/156 |
| 3,902,497 | 9/1975 | Casey | 128/296 |
| 3,961,629 | 6/1976 | Richter et al. | 128/296 |
| 3,993,074 | 11/1976 | Murray et al. | 128/286 |
| 4,061,145 | 12/1977 | DesMarais | 128/275 |
| 4,282,121 | 8/1981 | Goodrich | 260/17.4 GC |
| 4,333,461 | 6/1982 | Muller | 128/284 |
| 4,394,930 | 7/1983 | Korpman | 220/444 |
| 4,522,953 | 6/1985 | Barby et al. | 521/64 |
| 4,529,739 | 7/1985 | Scott et al. | 521/72 |
| 4,613,543 | 9/1986 | Dabi | 428/304.4 |
| 4,663,358 | 5/1987 | Hyon et al. | 521/64 |
| 4,725,628 | 2/1988 | Garvey et al. | 521/137 |
| 4,725,629 | 2/1988 | Garvey et al. | 521/137 |
| 4,731,391 | 3/1988 | Garvey | 521/137 |
| 4,740,528 | 4/1988 | Garvey et al. | 521/128 |
| 4,902,565 | 2/1990 | Brook | 428/315.5 |
| 4,962,172 | 10/1990 | Allen et al. | 526/318.42 |
| 4,985,467 | 1/1991 | Kelly et al. | 521/52 |
| 4,990,541 | 2/1991 | Nielsen et al. | 521/70 |
| 5,011,864 | 4/1991 | Nielsen et al. | 521/70 |
| 5,147,345 | 9/1992 | Young et al. | 604/378 |
| 5,149,720 | 9/1992 | DesMarais et al. | 521/63 |
| 5,164,421 | 11/1992 | Kiamil et al. | 521/159 |
| 5,189,070 | 2/1993 | Brownscombe et al. | 521/64 |
| 5,198,472 | 3/1993 | DesMarais et al. | 521/63 |
| 5,210,104 | 5/1993 | Bass et al. | 521/64 |
| 5,250,576 | 10/1993 | DesMarais et al. | 521/63 |
| 5,252,620 | 10/1993 | Elliott, Jr. et al. | 521/64 |
| 5,260,345 | 11/1993 | DesMarais et al. | 521/148 |
| 5,268,224 | 12/1993 | DesMarais et al. | 428/286 |
| 5,280,079 | 1/1994 | Allen et al. | 525/329.2 |
| 5,290,820 | 3/1994 | Brownscombe et al. | 521/64 |
| 5,292,777 | 3/1994 | DesMarais et al. | 521/64 |
| 5,328,935 | 7/1994 | Van Phan et al. | 521/64 |
| 5,331,015 | 7/1994 | DesMarais et al. | 521/62 |
| 5,338,766 | 8/1994 | Phan et al. | 521/63 |
| 5,352,711 | 10/1994 | DesMarais | 521/149 |
| 5,358,974 | 10/1994 | Brownscombe et al. | 521/64 |
| 5,362,761 | 11/1994 | Uragami et al. | 521/64 |
| 5,387,207 | 2/1995 | Dyer et al. | 604/369 |
| 5,500,451 | 3/1996 | Goldman et al. | 521/64 |
| 5,506,035 | 4/1996 | Van Phan et al. | 428/196 |
| 5,550,167 | 8/1996 | DesMarais | 521/50 |
| 5,563,179 | 10/1996 | Stone et al. | 521/64 |
| 5,573,994 | 11/1996 | Kabra et al. | 521/64 |

OTHER PUBLICATIONS

American Society for Testing Materials (ASTM) Designation: D 4032–82, "Standard Test Method for Stiffness of Fabric by the Circular Bend Procedure," pp. 702–706, published Aug. 1982.

Good, Robert J. and Robert J. Stromberg, Editors, Surface and Colloid Science–Experimental Methods, vol. II, Plenum Press, 1979, pp. 31–91.

*Primary Examiner*—Morton Foelak
*Attorney, Agent, or Firm*—John R. Schenian; Greg E. Croft

[57] ABSTRACT

Disclosed is a process for preparing an absorbent foam. The process generally comprises forming a solution of a polymer in a solvent, freezing the solution at a relatively slow cooling rate to a temperature below the freezing point of the solvent, removing the solvent from the frozen solution, and recovering the polymer to form a water-swellable, water-insoluble polymeric foam. The process has been found to enable one to prepare an absorbent foam that exhibits desirable softness and flexibility properties yet is highly absorbent. Such an absorbent foam may be used in a disposable absorbent product intended for the absorption of fluids such as body fluids.

18 Claims, 1 Drawing Sheet

PROCESS FOR PREPARING AN ABSORBENT FOAM

BACKGROUND OF THE INVENTION

1. Field of the Invention

The present invention relates to a process for preparing an absorbent foam. The process generally comprises forming a solution of a soluble polymer in a solvent, freezing the solution at a relatively slow cooling rate to a temperature below the freezing point of the solvent, removing the solvent from the frozen solution, and recovering the polymer to form a water-swellable, water-insoluble polymeric foam. The process has been found to enable one to prepare an absorbent foam that exhibits desirable softness and flexibility properties yet is highly absorbent. Such an absorbent foam may be used in a disposable absorbent product intended for the absorption of fluids such as body fluids.

2. Description of the Related Art

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

The use of water-swellable, generally water-insoluble absorbent materials, commonly known as superabsorbents, in disposable absorbent personal care products is known. Such absorbent materials are generally employed in absorbent products in order to increase the absorbent capacity of such products while reducing their overall bulk. Such absorbent materials are generally present in absorbent products in the form of small particles in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in water. Clearly, incorporation of such absorbent materials in disposable absorbent products can reduce the overall bulk while increasing the absorbent capacity of such products.

As an alternative to using a fibrous matrix containing superabsorbent materials, absorbent foams are also known. One form of an absorbent foam is wherein a foam material, such as polyurethane, is prepared to include a particulate superabsorbent material within the structure of the polyurethane foam. Alternatively, a particulate superabsorbent material is located between at least two layers of a polyurethane foam material to form a layered composite structure. While such foam structures may be useful absorbent materials in specific applications, they have not been shown to be optimal for use in disposable absorbent products because their absorptive properties tend to be limited. In particular, the foam material is such structures, such as polyurethane, generally does not have a sufficient absorptive ability to retain liquids. Therefore, although the particulate superabsorbent material in the foam structure may be able to retain a liquid, the overall capacity of the foam structure to absorb and retain a liquid is limited. Furthermore, the overall absorptive properties of the foam structure tend to be limited due to the relatively low surface area to mass ratio of the particulate superabsorbent material portion relative to the foam portion of the structure.

Absorbent foams are also known that are prepared comprising essentially all superabsorbent material. Typically, a blowing agent is used to form a foamed, water-swellable, polymeric liquid absorbent material. However, certain absorbent foams prepared using specific blowing agents have been found to have limited use for liquid absorption or liquid distribution. This is typically due to physical characteristics of the foam structure, which may include discontinuous channels, a too large average cell size, unacceptably wide cell size distribution, and/or capillary diameters that vary widely and randomly, that tend to result in undesirable absorptive rates and capacities and undesirable liquid distribution properties. In addition, known absorbent foams that are prepared comprising essentially all superabsorbent material have typically been found to have undesirable non-absorptive physical characteristics such as a lack of softness or being too brittle. Furthermore, many of the known foams are hydrophobic in nature and need treatment with a wetting agent or other suitable treatment steps to obtain a hydrophilic nature. Such undesirable non-absorptive physical characteristics of an absorbent foam tends to limit the usefulness of the absorbent foam in disposable absorbent products since such disposable absorbent products generally need to be sufficiently flexible to withstand the rigors of use by a consumer and also be sufficiently soft to be acceptably comfortable during use.

Thus, there is a continuing need for improvement of absorbent foams. In particular, there is a need for an absorbent foam which exhibits a relatively high absorptive liquid capacity yet which exhibits desirable softness and flexibility properties. In addition, there is a need for a process for preparing such an absorbent foam that is simple, safe, and cost-effective.

It is therefore an object of the present invention to provide a process for preparing an absorbent foam that is simple, safe, and cost-effective.

It is also an object of the present invention to provide a disposable absorbent product which includes an absorbent foam that exhibits a relatively high absorptive liquid capacity yet which exhibits desirable physical characteristics such as softness and flexibility properties.

SUMMARY OF THE INVENTION

The present invention concerns a process for preparing an absorbent foam.

One embodiment of such a process comprises forming a solution of a soluble polymer in a solvent, freezing the solution at a relatively slow cooling rate to a temperature below the freezing point of the solvent, removing the solvent from the frozen solution, and optionally treating the polymer to form a water-swellable, water-insoluble polymer.

Another embodiment of such a process comprises forming a solution gel of a crosslinked polymer in a solvent, freezing the solution gel at a relatively slow cooling rate to a temperature below the freezing point of the solvent and removing the solvent from the frozen solution gel, resulting in a water-swellable, water-insoluble absorbent polymer foam.

In another aspect, the present invention concerns a disposable absorbent product comprising the absorbent foam disclosed herein.

One embodiment of such a disposable absorbent product comprises a liquid-permeable topsheet, a backsheet attached to the liquid-permeable topsheet, and an absorbent foam of the present invention located between the liquid-permeable topsheet and the backsheet.

DETAILED DESCRIPTION OF THE PREFERRED EMBODIMENTS

Figure 1:
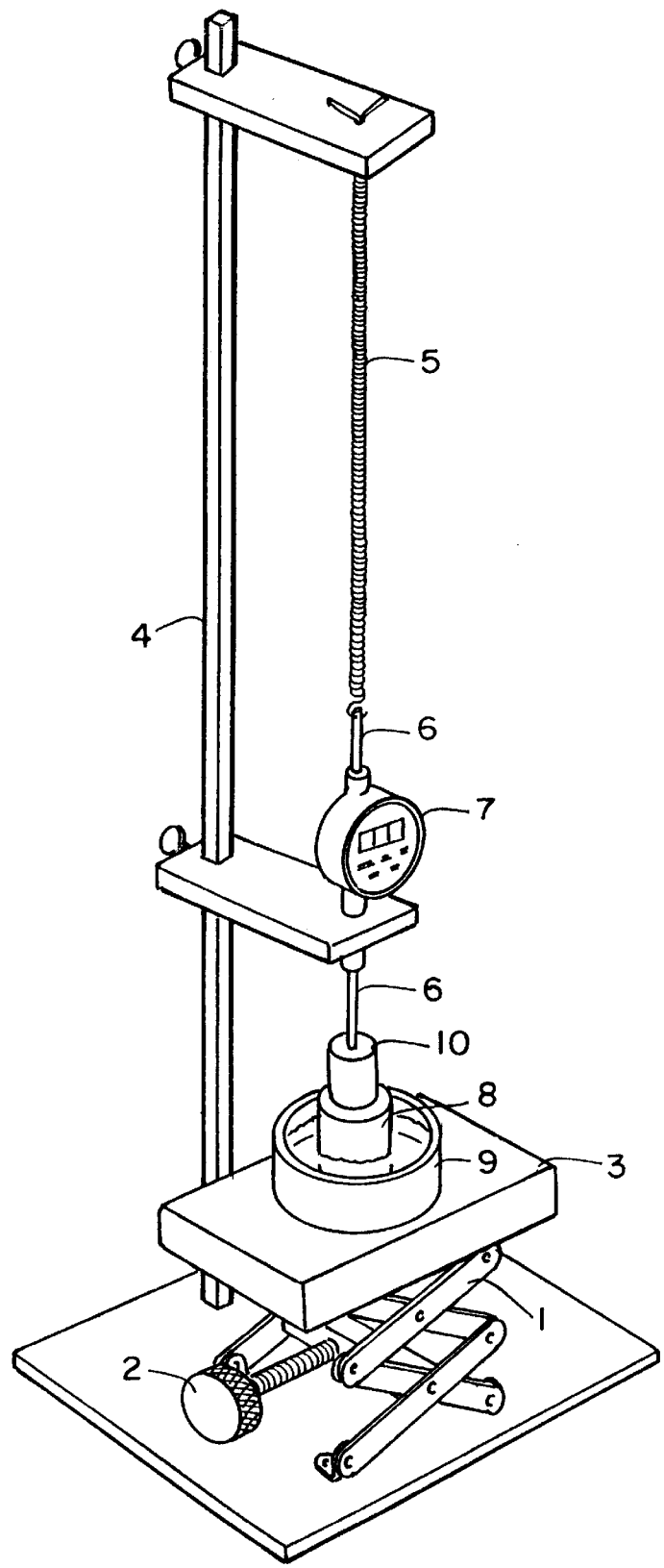
FIG. 1 is an illustration of the equipment employed in determining the Free Swell and Absorbency Under Load values of an absorbent foam or material.

The present invention is directed to an absorbent foam which exhibits a relatively high absorptive liquid capacity yet which exhibits desirable softness and flexibility properties. The absorbent foam comprises a water-swellable, water-insoluble polymer. As used in the present invention, the water-swellable, water-insoluble polymer to a large extent needs to provide the absorbent foam with its liquid-absorbing capacity. As such, the water-swellable, water-insoluble polymer needs to be effective to provide a desired amount of liquid-absorbing capacity to the absorbent foam.

As used herein, the term "foam" is generally intended to represent a porous polymeric matrix, which is an aggregate of hollow cells, the boundaries or walls of which cells comprise solid polymeric material. The cells may be interconnected to form channels or capillaries within the foam structure wherein such channels or capillaries facilitate liquid distribution within the foam.

As used herein, the term "water-swellable, water-insoluble" is meant to refer to a material that, when exposed to an excess of water, swells to its equilibrium volume but does not dissolve into the water. As such, a water-swellable, water-insoluble material generally retains its original identity or physical structure, but in a highly expanded state, during the absorption of the water and, thus, must have sufficient physical integrity to resist flow and fusion with neighboring materials.

As used herein, a material will be considered to be water soluble when it substantially dissolves in excess water to form a solution, thereby losing its initial form and becoming essentially molecularly dispersed throughout the water solution. As a general rule, a water-soluble material will be free from a substantial degree of crosslinking, as crosslinking tends to render a material water insoluble.

Polymers which are suitable for use in the present invention are generally any polymer which is initially soluble in a solvent such that the soluble polymer may be formed into a solution by mixing with a liquid solvent, such as water, and then whereby the polymer is treated to cause the polymer to become water-swellable and water-insoluble so that an absorbent foam comprising such water-swellable, water-insoluble polymer exhibits desired absorbency and physical characteristics.

Polymers which are suitable for use in the present invention include a wide variety of anionic, cationic, and nonionic materials. Suitable polymers include polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyacrylamides, polyquaternary ammoniums, natural based polysaccharide polymers such as carboxymethyl celluloses, carboxymethyl starchs, hydroxypropyl celluloses, algins, alginates, carrageenans, acrylic grafted starchs, acrylic grafted celluloses, chitin, and chitosan, and synthetic polypeptides such as polyaspartic acid, polyglutamic acid, polyasparagins, polyglutamines, polylysines, and polyarginines, as well as copolymers and mixtures of any of the foregoing polymers.

In one embodiment of the present invention, it is desired that the polymer used be a glassy polymer. As used herein, the term "glassy" polymer is meant to refer to a polymer having a glass transition temperature (Tg) above about 23° C. (about room temperature) at a relative humidity of about 30 percent or less. Examples of glassy polymers include, but are not limited to, sodium polyacrylate, polyacrylic acid, sodium carboxymethyl cellulose, and chitosan salt polymers. Examples of non-glassy polymers include, but are not limited to, polyethylene oxide, polyvinyl acetate, and polyvinyl ether polymers.

One property of the water-swellable, water-insoluble polymer which is relevant to its effectiveness in providing a desired amount of liquid-absorbing capacity to an absorbent foam is its molecular weight. In general, a water-swellable, water-insoluble polymer with a higher molecular weight will exhibit a higher liquid-absorbing capacity as compared to a water-swellable, water-insoluble polymer with a lower molecular weight.

The water-swellable, water-insoluble polymer useful in the absorbent foam of the present invention may generally have a wide range of molecular weights. A water-swellable, water-insoluble polymer having a relatively high molecular weight is often beneficial for use in the present invention. Nonetheless, a wide range of molecular weights is generally suitable for use in the present invention. Water-swellable, water-insoluble polymers suitable for use in the present invention will beneficially have a weight average molecular weight greater than about 10,000, more beneficially greater than about 100,000, even more beneficially greater than about 200,000, suitably greater than about 500,000, more suitably greater than about 1,000,000, and up to about 20,000,000. Methods for determining the molecular weight of a polymer are well-known in the art.

It is generally desired that the polymer be present in the absorbent foam in an amount effective to result in the absorbent foam exhibiting desired properties. The polymer will be present in the absorbent foam in a weight amount that is greater than 50 and up to 100 weight percent, beneficially between about 60 weight percent to about 100 weight percent, more beneficially between about 70 weight percent to about 100 weight percent, suitably between about 80 weight percent to about 100 weight percent, more suitably between about 90 weight percent to about 100 weight percent, and even more suitably between about 95 weight percent to about 100 weight percent, wherein all weight percents are based on the total weight amount of the polymer, any crosslinking agents, and any other optional components present in the absorbent foam. In one embodiment of the present invention, it is desired that the absorbent foam consist essentially of the polymer and any crosslinking agent used to crosslink the polymer. As will be appreciated by one skilled in the art, such an absorbent foam may also comprise an insubstantial amount of solvent retained from the preparation process and/or an insubstantial amount of water vapor absorbed from the air. In general, the presence of any materials in the absorbent foam that are not the water-swellable, water-insoluble polymer will tend to reduce the overall liquid absorbency capacity of the absorbent foam.

The water-swellable, water-insoluble polymer useful in the absorbent foam will generally be crosslinked. The amount of crosslinking should generally be above a minimum amount sufficient to make the polymer water-insoluble but also below some maximum amount so as to allow the polymer to be sufficiently water swellable so that the water-swellable, water-insoluble polymer absorbs a desired amount of liquid absorption.

Crosslinking of the polymer may generally occur either while the polymer is in solution or after the solvent has been removed from the solution used to prepare the absorbent foam. Such crosslinking of the polymer may generally be achieved by either of two different types of crosslinking agents. Such crosslinking agents will generally be soluble in the solvent being used, such as water.

One type of crosslinking agent is a latent crosslinking agent. Suitable latent crosslinking agents are generally either internal latent crosslinking agents or external latent crosslinking agents. An internal latent crosslinking agent is generally copolymerizable to the monomer or monomers used to prepare the polymer and, thus, generally comprise at least one vinyl group and one functional group or functionality that is capable of reacting with the side groups on the base polymer, such as a carboxyl group (—COO$^-$) on a sodium polyacrylate polymer or a carboxylic acid group (—COOH) on a polyacrylic acid polymer. Examples of suitable copolymerizable crosslinking agents include ethylenically unsaturated monomers, such as ethylene glycol vinyl ether and amino propyl vinyl ether.

An external latent crosslinking agent generally crosslinks the polymer itself after, for example, the polymer has been formed from the monomer or monomers used to prepare the polymer and/or the polymer has been mixed with a solvent to form a solution. Latent crosslinking agents generally do not take part in the overall polymerization process but, instead, are reactive to the polymer at a later point in time when a proper crosslinking condition is provided. Suitable post treatment conditions include using heat treatment, such as a temperature above about 60° C., exposure to ultraviolet light, exposure to microwaves, steam or high humidity treatment, high pressure treatment, or treatment with an organic solvent.

Suitable external latent crosslinking agents are any organic compound having at least two functional groups or functionalities capable of reacting with the carboxyl, carboxylic acid, amino, or hydroxyl groups of a polymer. It is desired that such an organic crosslinking agent be selected from the group consisting of diamines, polyamines, diols, and polyols and mixtures thereof; particularly from the group consisting of primary diols, primary polyols, primary diamines and primary polyamines and mixtures thereof. Of the diols and polyols, those possessing longer, such as 4 or greater, carbon chain lengths are generally beneficial. Specifically, the crosslinking agent may be selected from the group consisting of chitosan glutamate, type A gelatin, diethylenetriamine, ethylene glycol, butylene glycol, polyvinyl alcohol, hyaluronic acid, polyethylene imine and their derivatives and mixtures thereof. Other suitable organic crosslinking agents include monochloroacetic acid, sodium chloroacetate, citric acid, butane tetracarboxylic acid, and amino acids such as aspartic acid, and mixtures thereof. Another suitable latent crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$. Suitable metal ion crosslinking agents include those of the transition elements which generally have vacant d-orbitals. Suitable metal ion crosslinking agents include $AlCl_3$, $FeCl_3$, $Ce_2(SO_4)_3$, $Zr(NH_4)_4(CO_3)_4$ and $Ce(NH_4)_4(SO_4)_4 \cdot 2H_2O$, other well known metal ion compounds and mixtures thereof. Such metal ion crosslinking agents, when used with a particular polymer, are believed to form ionic bonds with the carboxyl, carboxylic, amino, or hydroxyl groups on the polymer. Metal ions with only two positive charges, such as $Zn^{2+}$, $Ca^{2+}$, or $Mg^{2+}$, are also suitable as crosslinking agents for certain polymers.

When the polymer is a cationic polymer, a suitable crosslinking agent is a polyanionic material such as sodium polyacrylate, carboxymethyl cellulose, or polyphosphate.

A second type of crosslinking mechanism that certain polymers are able to undergo involves a macromolecular rearrangement of the chains of the polymer during the solidification process of the polymer such that the polymer forms a higher ordered structure with a high degree of crystallinity which is generally water insoluble. Polymers suitable to such a crosslinking approach include, but are not limited to, polyvinyl alcohol, chitosan, and carboxymethyl cellulose with a lower degree of carboxymethylation. Additional strong bonding of the polymer could be established between the polymer chains during the solidification process which could result in a generally water insoluble material. An example of this behavior is the strong hydrogen bonding in polyvinyl alcohol forming an insoluble material. A closely related behavior is the formation of hard and soft segments in water soluble polyurethane materials which makes them water swellable but water insoluble.

Suitable crosslinking agents for a polymer solution gel process are also generally of two different types: either internal polymerizable or external crosslinking agent. The first type of crosslinking agent is a polymerizable but instant crosslinking agent. Suitable polymerizable crosslinking agents are generally reactive to the monomer or monomers used to prepare the polymer and, thus, generally comprise at least two functional groups or functionalities that are capable of reacting with the monomers. Examples of suitable polymerizable crosslinking agents include ethylenically unsaturated monomers, such as N,N'-methylene bis-acrylamide for free radical polymerization, and polyamines or polyols for condensation polymerization. The second type of crosslinking agent is a reactive compound having at least two functional groups or functionalities capable of reacting with the carboxyl, carboxylic acid, amino, or hydroxyl groups of a polymer in the solution stage wherein such crosslinking is not latent, in that no additional conditions are needed to initialize the crosslinking reaction. Suitable crosslinking agents may be selected from the group consisting of aldehydes, such as glutaraldehyde, or glycidyl ethers, such as polyethylene gylcol diglycidyl ether.

Another approach to form a crosslinked polymer network in either a polymer solution or on a recovered polymer is the use of a high energy treatment such as electron beam radiation or microwave radiation to form free radicals in the polymer which are then used to generate crosslinking points. This approach is applicable but not limited to instances where a crosslinking agent is not used to prepare the absorbent foam.

If a crosslinking agent is used, it is generally desired that the crosslinking agent be used in an amount that is beneficially from about 0.01 weight percent to about 20 weight percent, more beneficially from about 0.05 weight percent to about 10 weight percent, and suitably from about 0.1 weight percent to about 5 weight percent, based on the total weight of the polymer and the crosslinking agent present in an absorbent foam.

In general, a crosslinking catalyst will not be needed, but may be beneficial, to assist in the crosslinking of the polymer in order to prepare the absorbent foam of the present invention. For example, if citric acid is used as the crosslinking agent, sodium hypophosphite is beneficially used as a crosslinking catalyst. If a crosslinking catalyst is used, it is generally desired that the crosslinking catalyst be used in an amount of from about 0.01 to about 3 weight percent, suitably from about 0.1 to about 1 weight percent, based on the total weight of the polymer used.

While the principal components of the absorbent foam of the present invention have been described in the foregoing, such an absorbent foam is not limited thereto and can include other components not adversely effecting the desired properties of the absorbent foam. Exemplary materials which could be used as additional components would include, without limitation, pigments, antioxidants, stabilizers, plasticizers, nucleating agents, surfactants, waxes, flow promoters, solid solvents, particulates, and materials added to enhance processability of the absorbent foam. If such additional components are included in an absorbent foam, it is generally desired that such additional components be used in an amount that is beneficially less than about 5 weight percent, more beneficially less than about 3 weight percent, and suitably less than about 1 weight percent, wherein all weight percents are based on the total weight amount of the amount of the polymer, any crosslinking agents, and any other optional components present in the absorbent foam.

The absorbent foam of the present invention suitably has the ability to absorb a liquid, herein referred to as the Free Swell (FS) value. The method by which the Free Swell value is determined is set forth below in connection with the examples. The Free Swell values determined as set forth below and reported herein refer to the amount in grams of an aqueous solution, containing 0.9 weight percent sodium chloride, a gram of a material can absorb in about 1 hour under a negligible load of about 0.01 pound per square inch (psi). As a general rule, it is desired that the absorbent foam of the present invention has a Free Swell value, for a load of about 0.01 psi, of at least about 10, beneficially of at least about 15, more beneficially of at least about 20, suitably of at least about 25, more suitably of at least about 30, and up to about 200 grams per gram of absorbent foam.

The absorbent foam of the present invention also suitably has the ability to absorb a liquid while the absorbent composition is under an external pressure or load, herein referred to as the Absorbency Under Load (AUL) value. The ability of a material to absorb a liquid while the absorbent composition is under an external pressure or load has been found to often be an important characteristic of an absorbent material used in a disposable absorbent product since, while being worn and/or used by a consumer, the disposable absorbent product is often subjected to an external pressure or load that may negatively impact on the ability of the absorbent material being used to effectively absorb any liquid insulting the disposable absorbent product. The method by which the Absorbency Under Load is determined is set forth below in connection with the examples. The Absorbency Under Load values determined as set forth below and reported herein refer to the amount in grams of an aqueous solution, containing 0.9 weight percent sodium chloride, a gram of a material can absorb in about 1 hour under a load of about 0.3 pound per square inch (psi). As a general rule, it is desired that the absorbent foam of the present invention has an Absorbency Under Load value, for a load of about 0.3 psi, of at least about 10, beneficially of at least about 15, more beneficially of at least about 20, suitably of at least about 25, more suitably of at least about 30, and up to about 100 grams per gram of absorbent foam.

It has been discovered that the conditions under which an absorbent foam is stored may potentially have an impact on the absorbent properties of the absorbent foam as it ages. Even relatively mild conditions, such as ambient conditions, such as about 24° C. and at least about 30 percent relative humidity, suitably between about 30 to about 60 percent relative humidity, may result in a degradation of the absorbent properties of an absorbent foam as it ages. Typically, storage conditions, such as relatively higher temperatures and/or relatively higher relative humidities, as compared to ambient conditions, may result in quicker and/or more severe degradation of the absorbent properties of an absorbent foam as it ages.

In one embodiment of the present invention, the absorbent foam of the present invention will tend to retain its initial Free Swell and AUL values after aging. Specifically, an absorbent foam of the present invention may retain greater than about 50 percent, and suitably greater than about 70 percent, of its initial Free Swell or AUL values after aging for about 60 days. Typically, the aging conditions are at ambient conditions, such as at about 24° C. and at least about 30 percent relative humidity. For example, if an absorbent foam of the present invention has an initial AUL value of about 20, that absorbent foam may have an AUL value of at least about 10, and suitably of about 14, after aging for about 60 days at about 24° C. and at least about 30 percent relative humidity. Otherwise similar absorbent foams may tend to not retain their initial Free Swell or AUL values after aging under similar conditions.

Suitably, the absorbent foam of the present invention retains greater than about 50 percent, and more suitably greater than about 70 percent, of their initial Free Swell and AUL values after aging for about 60 days at about 24° C. and about 100 percent relative humidity.

As used herein, the term "initial Free Swell" or "initial Absorbency Under Load" is meant to refer to that Free Swell or AUL value exhibited by an absorbent foam as measured within about 1 day after preparation of the absorbent foam when the absorbent foam is stored at ambient conditions, such as at about 24° C. and between about 30 to about 60 percent relative humidity.

It is also desirable that the absorbent foam of the present invention exhibit addition liquid handling properties such as suitable liquid vertical wicking or liquid intake rate values.

The absorbent foam of the present invention also suitably exhibits desired softness characteristics, herein quantified by the use of a Softness value. It is generally desired to have an absorbent foam that is soft and flexible so that a disposable absorbent product comprising the absorbent foam will provide a good fit to a wearer or user of the disposable absorbent product so as to prevent premature liquid leakage, a certain degree of comfort, and a reduced packaging volume because a soft material generally provides a maximum compressibility and folding capacity. The method by which the Softness value is determined is set forth below in connection with the examples. The Softness values determined as set forth below and reported herein refer to the force value that relates to the stiffness of a material. Using the test method described herein, the Softness value of a material gives an average of the stiffness of the material in all directions, and is a measurement of force exerted on the material at a rate of 50 centimeters per minute, in a circular bending test. In general, the higher the force value needed to bend a material, the more stiff the material is. As a general rule, it is desired that the absorbent foam of the present invention exhibits a Softness value that is beneficially less than about 30, more beneficially less than about 25, even more beneficially less than about 20, suitably less than about 15, more suitably less than about 10, and even more suitably less than about 5 grams of force per gram per square meter of absorbent foam.

A typical foam will comprise open spaces or cells within the structure of the foam. In the development of the present invention, it has been determined that the size of the cells of an absorbent foam generally affects certain liquid transportation properties, such as vertical liquid wicking values, but that the size of the cells of an absorbent foam generally has a minimal affect on the overall softness or flexibility of the absorbent foam. Such has been found to be particularly true when the polymer being used to prepare the absorbent foam is a glassy polymer. Instead, the softness or flexibility of an absorbent foam has been found to be generally dependent on the thickness of the cell walls. In general, the thinner the wall thickness of the cells of an absorbent foam, the softer and/or more flexible the absorbent foam will be. In order to achieve the desired absorbency and physical characteristics of the absorbent foam of the present invention, it has been found that both the average cell size and the average thickness of the cell walls of an absorbent foam needs to be carefully controlled and, preferably, optimized.

In one embodiment of the present invention, it is generally desired that the average cell size of the cells in an absorbent foam beneficially be in the range of about 10 microns to about 100 microns and suitably in the range of about 10 microns to about 50 microns. Such a range of the average cell size of the cells in an absorbent foam has been found to generally result in an effective channel system for distributing liquid within the structure of the absorbent foam. The method by which the average cell size of the pores in an absorbent foam is determined is set forth below in connection with the examples.

In one embodiment of the present invention, it is generally desired that the average wall thickness of the cells in an absorbent foam beneficially be in the range of about 0.1 micron to about 30 microns and suitably in the range of about 0.5 micron to about 10 microns. Such a range of the wall thickness of the cells in an absorbent foam has been found to generally result in achieving desired physical properties, such as softness and/or flexibility, of the absorbent foam. The method by which the average wall thickness of the pores in an absorbent foam is determined is set forth below in connection with the examples.

As used herein, the term "hydrophobic" refers to a material having a contact angle of water in air of at least 90 degrees. In contrast, as used herein, the term "hydrophilic" refers to a material having a contact angle of water in air of less than 90 degrees. For the purposes of this application, contact angle measurements are determined as set forth in Robert J. Good and Robert J. Stromberg, Ed., in "Surface and Colloid Science—Experimental Methods", Vol. II, (Plenum Press, 1979). The absorbent foam of the present invention are generally hydrophilic as prepared and therefore generally do not require any subsequent treatment to make them hydrophilic. This is in contrast to many absorbent foams known in the art in which the polymeric material of the foam is not inherently hydrophilic but is rendered hydrophilic by a suitable treatment, such as by the addition of a surfactant.

The absorbent foam of the present invention has been found to be able to be prepared by a relatively simple, safe, and cost-effective process. In one embodiment, the process generally comprises forming a solution of a soluble polymer in a solvent, freezing the solution at a relatively slow cooling rate to a temperature below the freezing point of the solvent, removing the solvent from the frozen solution, and optionally treating the polymer to form a water-swellable, water-insoluble polymeric absorbent foam.

In another embodiment, the process comprises forming a solution of monomers in a solvent, polymerizing the monomers to form a solution gel of a crosslinked polymer in the solvent, freezing the solution gel at a relatively slow cooling rate to a temperature below the freezing point of the solvent, and removing the solvent from the frozen solution gel. Optionally, the solution gel of the crosslinked polymer could be subjected to additional swelling, by using additional solvent, before freezing the solution gel.

The absorbent foam of the present invention is also believed to be capable of being formed by a process generally comprising forming a solution of a soluble polymer in a solvent, adding a blowing agent to the solution, initiating the blowing agent, removing the solvent from the solution, and optionally treating the polymer to form a water-swellable, water-insoluble polymeric absorbent foam.

As used herein, the term "solvent" is intended to represent a substance, particularly in a liquid form, that is capable of dissolving the polymer used herein to form a substantially uniformly dispersed mixture at the molecular level. In the present invention, the solvent used to prepare the absorbent foam needs to be capable of first freezing and then be capable of undergoing sublimation, wherein the solvent passes directly from its frozen state to a vapor state. As such, the solvent used to prepare the absorbent foam should have a freezing point at which the solvent changes from a liquid to a solid. The freezing point of water and other solvents is generally well known in the art. However, as will be recognized by one skilled in the art, the freezing point of a particular solvent may be affected by such factors as the particular solvent, polymer and the crosslinking agents being used as well as the relative concentrations of the respective components in the solution.

The soluble polymer or the monomers are typically dissolved in a solvent comprising at least about 30 weight percent water, beneficially about 50 weight percent water, suitably about 75 weight percent water, and more suitably 100 weight percent water. When a co-solvent is employed with the water, other suitable solvents include methanol, ethanol, acetone, isopropyl alcohol, ethylene glycol, glycerol, and other solvents known in the art. However, when a water-soluble polymer is used, the use or presence of such other, non-aqueous solvents may impede the formation of a homogeneous mixture such that the polymer does not effectively dissolve into the solvent to form a solution.

In general, a solution of the polymer, the solvent and, optionally, a crosslinking agent and/or other optional components is prepared, wherein the polymer may be added to the solution as a polymer or formed as a polymer in the solution from monomers. In the present invention, it has been discovered that controlling the concentration of the polymer in the solution is important to achieving an absorbent foam that exhibits the desired properties. In general, if the concentration of the polymer in the solution is too high, the resultant absorbent foam prepared has been found to not exhibit the desired properties, particularly softness, due to the formation of relatively thick cell walls. Without intending to be bound hereby, it is hypothesized that the use of too great of a concentration of the polymer in the solution results in a relatively small volume of space occupied by solvent molecules as compared to the overall solution volume. In general, if the concentration of the polymer in the solution is too low, the resultant absorbent foam prepared has been found to not exhibit the desired properties, particularly absorbent properties and liquid distribution capability, due to the formation of cell walls that are too thin and cells that are too large. Without intending to be bound hereby, it is hypothesized that the use of too small of a concentration of the polymer in the solution results in too much volume of space occupied by the solvent molecules. It has generally been found that the higher the concentration of the polymer in the solution, the resulting absorbent foam exhibits a smaller average cell size and thicker average cell walls as compared to an absorbent foam prepared from a solution with a lower concentration of the polymer in the solution.

Thus, it is generally desired that the solution comprises from about 0.1 to about 30 weight percent, beneficially from about 0.5 to about 20 weight percent, and suitably from about 1 to about 10 weight percent, based on total solution weight, of the polymer. The solution generally comprises from about 99.99 to about 70 weight percent, beneficially from about 99.5 to about 80 weight percent, and suitably from about 99 to about 90 weight percent of the solvent.

In one embodiment of the present invention, the dissolution of the soluble polymer into the solvent is believed to result in entanglement of individual segments of the polymer chains with each other. Such entanglement results in the polymer chains interpenetrating one another in the mixture, so that a random, coil-entangled molecular configuration occurs which is believed to effectively provide crosslinking points and which assists allowing for additional crosslinking of the polymer upon further treatment as, for example, with heat-treatment. To allow for effective entanglement of individual segments of the polymer with each other, the solution is suitably allowed to form a stable, homogeneous solution at equilibrium prior to additional treatment steps to ensure effective dissolution of the polymer into the solvent. It will be appreciated that a relatively minor amount of a non-soluble portion of the polymer may exist that will typically not dissolve into the solvent. For example, the retained crystalline areas of a crystalline-crosslinked polymer will typically not dissolve in water while the non-crystalline areas typically will.

Generally, the order of mixing the polymer or monomers, the solvent and, optionally, any crosslinking agents is not critical. As such, either the polymer, the monomers, or the crosslinking agent may be added to the solvent and then the remaining component subsequently added, or all components may be added together at the same time. However, it may be beneficial, when using certain crosslinking agents, to first add the polymer or monomer and solvent and then to add the crosslinking agent to the solution.

The solution of the polymer or monomers, solvent and, optionally, a crosslinking agent can generally be formed at any temperature at which the polymer or monomers is soluble in the solvent. Generally, such temperatures will be within the range of from about 10° C. to about 100° C.

The solution may be acidic (a pH of less than 7), neutral (a pH of 7), or basic (a pH greater than 7). If desired, the solution can be acidified by the addition of an aqueous solution of an inorganic acid, such as hydrochloric acid or nitric acid, or an aqueous solution of an organic acid, such as acetic acid. Similarly, if it is desired to provide the solution with a basic pH, a base such as an aqueous solution of sodium hydroxide, potassium hydroxide, or ammonia can be added to the solution.

The solution will generally have a pH within the range of from about 2 to about 12, beneficially from about 4 to about 9, more beneficially from about 4 to about 7.5, and suitably from about 6 to about 7.5. The resulting absorbent foam will generally have the same pH as the solution.

When the absorbent foam of the present invention is intended for use in personal care products, such as diapers, training pants, and feminine care products, it is typically desired that the absorbent foam have a generally neutral character. For this reason, it is generally beneficial that the solution be formed with a generally neutral pH. If the solution is formed with an acidic or basic pH, the recovered absorbent foam may be acidic or basic (respectively) but may be neutralized. A recovered absorbent foam which is acidic may be neutralized, for example, by contacting it with a gaseous base such as ammonia. A recovered absorbent foam which is basic may be neutralized, for example, by contacting it with an acidic gas such as carbon dioxide.

After forming the solution comprising the polymer or monomers, solvent and, optionally, a crosslinking agent, the solution is beneficially agitated, stirred, or otherwise blended to effectively uniformly mix the components such that an essentially homogeneous solution is formed.

If monomers are being used, the monomers are suitably then treated to form the desired polymer in the solution.

The solution is then cooled to a temperature that is below the freezing point of the solvent such that the solvent freezes and becomes a solid phase in the solution. Since the polymer and, optionally, a crosslinking agent are essentially homogeneously dispersed in the solution, it is generally desired that the polymer and, optionally, the crosslinking agent form an essentially continuous matrix within the frozen solution when the solvent freezes and becomes a solid phase. As such, the essentially continuous matrix of the polymer and, optionally, the crosslinking agent will become substantially encased by the frozen solvent, forming an essentially uniform bicontinuous structure. As used herein, the term "encase" and related terms are intended to mean that the frozen solvent phase substantially encloses or surrounds the essentially continuous matrix of the polymer and, optionally, the crosslinking agent.

As will be recognized by one skilled in the art, the temperature to which the solution is cooled in order to freeze the solvent will typically depend on such factors as the solvent, the polymer and the crosslinking agent being used as well as the relative concentrations of the respective components in the solution. In general, it has been found that if the temperature to which to solution is eventually cooled is too close to the freezing point of the solvent, the frozen polymer solution may not exhibit sufficient strength and may deform under further processing steps such as under vacuum treatment to remove the frozen solvent. In addition, the freezing point of the solvent may be depressed due to the effect of the dissolved polymer and/or crosslinking agent. As such, if the solution is merely cooled to the freezing point of the pure solvent, then some of the solvent present in the solution may not be in the frozen state at such a temperature. In general, it has also been found that if the temperature to which to solution is eventually cooled is too far below the freezing point of the solvent, molecules of the solvent in the solution may tend to form a non-uniform crystalline phase throughout the solution which has been found to often cause the formation of cracks in the polymer matrix and thus in the absorbent foam that is being prepared. Such cracks tend to reduce the mechanical properties of the absorbent foam, such as tensile strength and softness or flexibility. In addition, the use of very low temperatures tends to slow down the rate of subliming the frozen solvent.

In the situation where the solvent used to prepare the absorbent foam is essentially all water or an aqueous solution comprising mostly water but also other solvents, it is generally desired that the temperature to which to solution is eventually cooled to be between about −50° C. and about 0° C., beneficially between about −50° C. and about −5° C., more beneficially between about −40° C. and about −10° C., and suitably between about −30° C. and about −10° C.

It has also been found that the rate at which the solution is cooled from a temperature above the freezing point of the solvent to a temperature below the freezing point of the solvent is important to achieving an absorbent foam that exhibits the desired properties described herein. In a qualitative manner, the cooling rate used should be not be so fast that visible cracks or visible non-uniformities begin to form in the freezing solution. As such, there is generally a critical cooling rate that will exist for a particular solution in order to achieve a desired absorbent foam of the present invention. Using a cooling rate that is faster than such a critical cooling rate will generally result in an undesirable absorbent foam that exhibits a relatively non-uniform pore structure and cracked polymer matrix. In contrast, using a cooling rate that is slower than such a critical cooling rate will generally result in a desirable absorbent foam that has a relatively uniform pore structure and the absence of any significant cracks or deformities in the polymer matrix.

As with the freezing point of a solvent, the critical cooling rate to be used for a particular solution will typically depend on such factors as the solvent, the polymer and the crosslinking agent being used as well as the relative concentrations of the respective components in the solution. In one embodiment of the present invention, wherein water is the solvent and the polymer is used in a concentration of between about 0.5 to about 2 weight percent, wherein the weight percent is based on the total weight of the solvent, the critical cooling rate has been found to be a decrease in temperature between about 0.4° C. to about 0.5° C. per minute. In such an embodiment, it is therefore desired that the cooling rate used to freeze the solvent be less than about 0.4° C. per minute, beneficially less than about 0.3° C. per minute, and suitably less than about 0.1° C. per minute.

As will be recognized by one skilled in the art, besides the approach using a cooling rate slower than a critical cooling rate to achieve an essentially uniform cell structure in the absorbent foam, other methods can also be applied. Such other methods include, but are not limited to, the inclusion of tiny air bubbles or the use of a nucleating agent. Without intending to be bound hereby, it is hypothesized that the use of a nucleating agent will increase the number of nuclei to ensure an essentially uniform crystallization of solvent molecules during the cooling process. Use of a nucleating agent generally increases the critical cooling rate.

After the solution has been cooled such that the solvent freezes and becomes a solid phase in the solution and the solution has beneficially reached a relatively stable temperature, the frozen solvent is then substantially removed from the solution. In the present invention, the use of a suitable vacuum to sublime the frozen solvent has been found to generally result in a desired absorbent foam. As will be appreciated by one skilled in the art, the vacuum to be used for a particular frozen solution will typically depend on such factors as the solvent, the polymer and the crosslinking agent being used, the relative concentrations of the respective components in the solution, and the temperature of the frozen solution. Desirable vacuum conditions are beneficially less than about 500 millitorrs, more beneficially less than about 300 millitorrs, suitably less than about 200 millitorrs, and more suitably less than about 100 millitorrs. In general, the higher the vacuum, the faster the rate of sublimation of the frozen solvent.

As used herein, the sublimation, by use of a vacuum, of the frozen solvent from the frozen solution is meant to represent that substantially all of the solvent is removed from the frozen solution prior to, if needed, any additional treatment steps. It will be appreciated, however, that even after removal of substantially all of the solvent, a small amount of solvent may remain entrapped within the structure of the remaining polymeric matrix. The amount of solvent remaining entrapped within the structure of the polymeric matrix will typically depend on the method and conditions under which the frozen solvent is sublimed. Generally, less than about 20 weight percent, beneficially less than about 15 weight percent, and suitably less than about 10 weight percent, of the original amount of solvent in the solution will remain entrapped within the remaining polymeric matrix of the absorbent foam.

After the frozen solvent has been substantially sublimed from the frozen solution, the polymer and, optionally, any crosslinking agent will remain, with the polymer generally forming a polymeric matrix comprising generally interconnected cells to achieve a foam structure. The polymeric matrix forms the walls of the cells with the open cells having been created by the sublimation of the frozen solvent. As discussed hereinbefore, it is generally desired that the resultant foam structure exhibit a desired average pore size and a desired average thickness of the cell walls.

The recovered foam structure may already exhibit the desired absorbent and physical properties such that the recovered foam structure is an absorbent foam of the present invention and does not require any further treatment steps. As will be appreciated by one skilled in the art, this will generally depend on the particular polymer and, if used, the particular crosslinking agent used in the preparation of the foam. Methods of preparation wherein the recovered foam structure may already exhibit the desired absorbent and physical properties include wherein monomers were polymerized in the solution to form a crosslinked and thus insoluble polymer gel solution; a crosslinking agent that is capable of reacting with the polymer at a relatively low temperature, such as at about room temperature or less, is used; and the polymer used, such as polyvinyl alcohol or chitosan, is capable of forming a highly ordered structure during the freezing and solidification process.

If the recovered foam structure does not yet exhibit the desired absorbent and physical properties, it may be necessary to treat the recovered polymeric foam structure with an additional process step. For example, if the crosslinking agent used is a latent crosslinking agent, such a crosslinking agent may not yet have reacted with the polymer because the proper crosslinking condition has not yet been provided to the polymer and crosslinking agent mixture. As such, an effective crosslinking condition may still need to be provided in order to crosslink the polymer to achieve a water-insoluble, water-swellable polymer. Suitable post treatment conditions include using heat treatment, exposure to ultraviolet light, exposure to microwaves, exposure to an electron beam, steam or high humidity treatment, high pressure treatment, or treatment with an organic solvent.

In general, if heat-treatment is necessary, any combination of temperature and time which is effective in achieving a desired degree of crosslinking, without undesirable damage to the polymer, so that the polymer and the absorbent foam exhibit the desired properties described herein, is suitable for use in the present invention. As a general rule, when a crosslinking agent is used, the polymer will be heat-treated at a temperature between about 50° C. to about 250° C., beneficially from about 80° C. to about 250° C., more beneficially from about 100° C. to about 200° C., and suitably from about 100° C. to about 160° C. The higher the temperature employed, the shorter the period of time generally necessary to achieve the desired degree of crosslinking. It has been found that if very high temperatures are used with an effective length of time, such as a temperature between about 100° C. and about 250° C. for a length of time between about 50 seconds and about 500 minutes, effective Free Swell and Absorbency Under Load values may be achieved for certain polymers, such as carboxyalkyl polysaccharide without the use of a crosslinking agent.

Generally, the heat-treating process will extend over a time period within the range of from about 1 minute to about 600 minutes, beneficially from about 2 minutes to about 200 minutes, and suitably from about 5 minutes to about 100 minutes.

If used, a heat-treating process, or any other acceptable post-recovery treatment process, generally causes the polymer to crosslink or additionally crosslink and become generally water swellable and water insoluble. Without intending to be bound hereby, it is believed that the post-recovery treatment processes cause the polymer to undergo a degree of crosslinking, not related to the presence of a crosslinking agent, through the formation of crosslinks between either the functional groups from the polymer and the external crosslinking agent or between the functional groups on the polymer when it contains more than one type of functional groups. One example of a self-crosslinkable polymer is carboxymethyl cellulose, which contains both carboxylic acid groups and hydroxyl groups and is able to form ester linkages. This self-crosslinking may be in addition to any crosslinking caused by the presence of a crosslinking agent. Further, when the crosslinking agent is a diamine or polyamine, it is believed that crosslinking occurs through amidation of any carboxyl groups on the polymer through the formation of an ammonia salt. Esterification, through a self-crosslinking process, is believed to occur primarily under a weakly acidic, neutral, or slightly basic condition. Esterification, through a self-crosslinking process, is not believed to proceed to a significant degree under relatively basic conditions. Crosslinking due to the crosslinking agent may occur under both acidic and basic conditions. Thus, the presence of the crosslinking agent allows for crosslinking to occur over a broad pH range.

There is generally an optimum degree or amount of crosslinking of a particular polymer that optimizes the absorbency properties of the particular crosslinked polymer. If too little crosslinking occurs, the polymer may possess relatively low absorbency properties, such as Absorbency Under Load values, due to a lack of gel strength. If too much crosslinking occurs, the polymer may similarly possess relatively low absorbency properties, such as Free Swell values, due to the inability of the polymer to absorb liquid.

Those skilled in the art will recognize that the presence of crosslinks formed by esterification or amidation, ionic bonding, or other types of linkages can be detected through various analytical techniques. For example, infrared spectroscopy and nuclear magnetic resonance can be used to verify the presence of ester and amide crosslinks.

The absorbent foams of the present invention are suited for use in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the absorbent foams of the present invention.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the absorbent structure comprises an absorbent foam of the present invention.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Test Methods

Free Swell

The Free Swell Capacity (FS) is a test which measures the amount in grams of an aqueous solution, containing 0.9 weight percent sodium chloride, a gram of a material can absorb in 1 hour under a negligible applied load or restraining force, such as of about 0.01 pound per square inch.

Referring to FIG. 1, the apparatus and method for determining the Free Swell and the Absorbency Under Load will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the absorbent foam material sample to be tested, has a liquid-permeable bottom and rests within a Petri dish 9 which contains the saline solution to be absorbed. For the determination of Absorbency Under Load values only, a weight 10 rests on top of a spacer disc (not visible) resting on top of the absorbent foam material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 5 (available from McMaster-Carr Supply Co., Chicago, Ill., Item No. 9640K41), which serves to counter or reduce the downward force of the probe to about 1 gram +0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, an absorbent foam material sample was cut into circular discs with a diameter of about one inch. A total of about 0.160 gram of the absorbent foam material sample, typically about 3 to 4 circular disc layers, is placed into the sample cup. The sample is then covered with a plastic spacer disc, weighing 4.4 grams and having a diameter of about 0.995 inch, which serves to protect the sample from being disturbed during the test and also to uniformly apply a load on the entire sample. The sample cup, with material sample and spacer disc, is then weighed to obtain its dry weight. The sample cup is placed in the Petri dish on the platform and the laboratory jack raised up until the top side of the plastic spacer disc contacts the tip of the probe. The meter is zeroed. A sufficient amount of saline solution is added to the Petri dish (50–100 milliliters) to begin the test. The distance the plastic spacer disc is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after about 1 hour is the Free Swell value expressed as grams saline solution absorbed per gram of absorbent foam sample. If desired, the readings of the modified thickness meter can be continuously inputted to a computer (Mitutoyo Digimatic Miniprocessor DP-2 DX) to make the calculations and provide Free Swell readings. As a cross-check, the Free Swell can also be determined by determining the weight difference between the sample cup before and after the test, the weight difference being the amount of solution absorbed by the sample.

Absorbency Under Load

The Absorbency Under Load (AUL) is a test which measures the amount in grams of an aqueous solution, containing 0.9 weight percent sodium chloride, a gram of a material can absorb in 1 hour under an applied load or restraining force of about 0.3 pound per square inch. The procedure for measuring the Absorbency Under Load value of an absorbent composition is essentially identical to the procedure for measuring the Free Swell values, except that a 100 gram weight is placed on top of the plastic spacer disc, thereby applying a load of about 0.3 pound per square inch onto the absorbent foam as it absorbs the saline solution.

Softness

The Softness value of a material is determined by a test which is modeled after the ASTM D4032-82 Circular Bend Procedure. This modified test is used for the purposes of the present invention and is, hereinafter, simply referred to as the "Circular Bend Procedure". The Circular Bend Procedure is a simultaneous multi-directional deformation of a material in which one face of a material becomes concave and the other face becomes convex. The Circular Bend Procedure gives a force value which relates to the stiffness of the material, simultaneously averaging stiffness in all directions, and is herein as being inversely related to the softness of the material.

The apparatus necessary for the Circular Bend Procedure is a modified Circular Bend Stiffness Tester, having the following parts: A smooth-polished steel plate platform which is 102.0 millimeters (length) by 102.0 millimeters (width) by 6.35 millimeters (depth) having a 18.75 millimeter diameter orifice. The lap edge of the orifice should be at a 45 degree angle to a depth of 4.75 millimeters. A plunger having the following dimensions is used: overall length of 72.2 millimeters, a diameter of 6.25 millimeters, a ball nose having a radius of 2.97 millimeters and a needle-point extending 0.88 millimeters from the ball nose with a 0.33 millimeter base diameter and a point having a radius of less than 0.5 millimeters. The plunger is mounted concentrically with the orifice having equal clearance on all sides. The needle-point is used merely to prevent lateral movement of a sample during testing. The bottom of the plunger should be set well above the top of the orifice plate. From this position, the downward stroke of the ball nose is to the exact bottom of the plate orifice.

An inverted compression load cell having a load range of from about 0.0 to about 2000.0 grams was used as a force measurement gauge. The compression tester used was an Instron Model No. 1122 inverted compression load cell, available from Instron Engineering Corporation of Canton, Massachusetts.

After calibrating the load cell, the gage length for displacement of the plunger was set to 25.4 mm. To carry out the test, an absorbent foam sample was cut into a 38.1×38.1 mm square specimen using a die cutter. The sample was placed onto the test platform and the plunger was lowered down on the specimen for a 25.4 mm gage length at a crosshead speed of 500 mm/min. During the movement of the plunger, the absorbent foam sample is deflected downward into the 18.75 mm hole by the plunger and the force exerted by the compression tester to deflect the foam sample during the 25.4 mm gage length displacement of the plunger is measured by the load cell and recorded. The force measured by the load cell divided by the basis weight of the specimen is reported in units of grams force/grams per square meter of specimen (g/gsm). This value is used as the Softness value to obtain a quantitative measure of the softness of the specimen. The higher the Softness value (in g/gsm), the more stiff and, thus, the less soft, the specimen.

Cell Pore Size and Cell Wall Thickness Measurements

A foam sample was cut by a sharp razor. The cut foams were attached to metal stubs using copper tape and imaged in an environmental scanning electron microscope using 12 kV beam voltage. The instrument used was an environmental scanning electron microscope, model E-2020 from Electroscan Corporation of Wilmington, Mass. The sample chamber pressure was about 1.2 Torr. The environmental backscatter electron detector was used to collect images, having the advantage of being able to discern any variations in composition. Magnification varied depending on the scale of the subject sample, with a 150 magnification used for a general survey of the sample and a 2500 magnification used to measure cell wall thickness and cell size. Cell wall thickness and cell size measurements were taken directly on the environmental scanning electron microscope. It was not possible to apply automated image analysis routines to these complex structures for cell wall thickness measurement. Manual measurement is required. The cell wall thickness and cell size of each sample are averaged from at least 20 measurements.

EXAMPLES

For use in the following examples, the following polymer materials were obtained.

Polymer 1: A carboxymethylcellulose having a weight average molecular weight greater than 1,000,000 and a degree of substitution of carboxymethyl groups on the anhydroglucose unit of the cellulosic material of about 0.7 was obtained from Aqualon of Wilmington, Del., a subsidiary of Hercules Inc., under the designation B313 carboxymethylcellulose. Carboxymethylcellulose is an anionic polymer.

Polymer 2: A sodium polyacrylate polymer having a weight average molecular weight of about 4,000,000 and degree of neutralization of about 70 percent was obtained from Polysciences of Warrington, Pa., under the catalog number of 06501. Sodium polyacrylate polymer is an anionic polymer.

Polymer 3: A sodium polyacrylate polymer having a weight average molecular weight of about 240,000 and degree of neutralization of about 70 percent was obtained from Polysciences of Warrington, Pa., under the catalog number of 18613. Sodium polyacrylate polymer is an anionic polymer.

Polymer 4: A sodium polyacrylate polymer having a weight average molecular weight of about 60,000 and degree of neutralization of about 70 percent was obtained from Polysciences of Warrington, Pa., under the catalog number of 18611. Sodium polyacrylate polymer is an anionic polymer.

Polymer 5: A chitosan acetate having a weight average molecular weight of about 11,000,000 and degree of acetylation of about 80 percent was obtained from Vanson Company of Seattle, Wash., under the designation VNS-608 chitosan. Chitosan acetate is a cationic polymer.

Polymer 6: A polyethyleneoxide having a weight average molecular weight of about 4,000,000 was obtained from Union Carbide Corporation of Danbury, Conn., under the designation WSR-301 polyethyleneoxide. Polyethyleneoxide is a nonionic polymer.

Example 1

Weight amounts of the various polymer samples were dissolved in separate batches of about 2000 grams of distilled water at a temperature of about 23° C. For the carboxymethylcellulose (Polymer 1) and polyethylene oxide (Polymer 6) solutions, about 0.2 gram of citric acid was also added to the solutions as a crosslinking agent. For the sodium polyacrylate solutions (Polymers 2–4) solutions, about 0.75 gram of an aqueous solution comprising about 40 weight percent of ammonium zirconium carbonate was also added to the solutions as a crosslinking agent. The various solutions were blended for about 2 to 3 hours to ensure thorough mixing of the components. About 500 grams of each prepared solution was placed into separate stainless steel pans, wherein the pans had dimensions of 10 inches (width) by 20 inches (length) by 1 inch (depth). The pans, containing the respective solutions, were then placed in a freeze dryer, available from The VirTis, Inc., of Gardiner, N.Y., under the designation VirTis Genesis model 25EL freeze dryer. The various solutions in the pans were then cooled down to about −15° C. at various cooling rates in order to freeze the water in the solutions. The various solutions in the pans were maintained at about −15° C. for about an hour to ensure substantially complete freezing of the water. The frozen solutions were left in the freeze dryer and then subjected to a vacuum of about 105 millitorrs, provided by a vacuum pump which had a condenser set to a temperature of about −60° C. to about −70° C., for about 15 hours. The resultant foam structures were then treated at various temperatures for various periods of time in order to assist in the crosslinking of the polymers. The final foam structures were then evaluated for Free Swell, Absorbency Under Load, and Softness values. The various process conditions and results of the evaluations for the various samples are summarized in Table 1. The foam sample prepared using Polymer 4 (Sample 7) was water soluble and therefore did not exhibit any measurable Free Swell and Absorbency Under Load values.

A comparative foam sample (Sample 10) was also prepared, as follows. About 250 grams of aqueous acrylic acid solution containing 50 percent by weight of acrylic acid was neutralized using 1 N sodium hydroxide solution to form sodium acrylate solution with 75 percent degree of neutralization. The neutralization was carried out slowly using an ice bath taking care to maintain the solution temperature around 5° C. to avoid any polymerization. About 200 ml of this solution was transferred to a 2 liter reaction vessel fitted with a heating jacket and a high shear mixer (Ultra-Turrax T25 mixer from Janke & Kunkel GmbH of Staufen, Germany). To the solution in the reaction vessel was added 0.5 grams of N,N'-methylenebisacrylamide, about 1.3 grams of 2,2'-azobis-(2-amidopropane) hydrochloride from Monomer-Polymer & Dajac Laboratories, Inc. of Feasterville, Pa., and about 20 grams of polyethylene glycol of 600 weight average molecular weight from Union Carbide Company maintaining the mixture at 22° C. About 3.5 grams of sorbitan monolaurate and about 6.5 grams of ethoxylated sorbitan monolaurate were mixed in about 60 grams of 1,1,2-trichlorotrifluoroethane and this mixture was then added to the solution in the reaction vessel. The high shear mixer was started and the mixture was mixed at a speed of about 8000 rpm for about 10 minutes after which the mixer was removed from the reaction vessel and the temperature increased to about 60° C. and maintained for about 1 hour to form the foam, followed by increasing and maintaining the temperature at about 80° C. for about 30 minutes and finally increasing and maintaining the temperature at about 120° C. for about 30 minutes. The reactor was then cooled to about 22° C. A mixture consisting of about 5 grams of glycerol and about 25 grams of isopropyl alcohol was added to the foam in the reactor and the temperature was increased to about 180° C. and maintained for about 1 hour. The reactor was then cooled to ambient temperature, the foam removed from the reactor and placed in a chamber at about 80 percent relative humidity for about 6 hours to obtain the final foam material. This foam sample was then evaluated for Free Swell, Absorbency Under Load, and Softness values, with the results of such evaluations also summarized in Table 1.

TABLE 1

| Sample No. | Polymer Type | Polymer Concentration (Weight Percent) | Cooling Rate | Heat Treatment Conditions (Temperature/Time) | Free Swell Value (g/g) | Absorbency Under Load Value (g/g) | Softness Value (g/gsm) |
| --- | --- | --- | --- | --- | --- | --- | --- |
| Sample 1 | Polymer 1 | 0.5 | 0.03° C./min | 130° C./10 min | 26.1 | 18.3 | 2.90 |
| Sample 2 | Polymer 1 | 0.5 | 0.2° C./min | 130° C./10 min | 21.8 | — | 6.53 |

TABLE 1-continued

| Sample No. | Polymer Type | Polymer Concentration (Weight Percent) | Cooling Rate | Heat Treatment Conditions (Temperature/Time) | Free Swell Value (g/g) | Absorbency Under Load Value (g/g) | Softness Value (g/gsm) |
|---|---|---|---|---|---|---|---|
| Sample 3 | Polymer 1 | 0.5 | 0.4° C./min | 130° C./10 min | 22.1 | — | 20.58 |
| *Sample 4 | Polymer 1 | 4.0 | 0.4° C./min | 130° C./10 min | 18.7 | — | 45.93 |
| Sample 5 | Polymer 2 | 0.5 | 0.03° C./min | 200° C./40 min | 35.0 | 19.5 | 1.36 |
| Sample 6 | Polymer 3 | 0.5 | 0.03° C./min | 200° C./5 hours | 42.8 | 2.5 | 1.09 |
| *Sample 7 | Polymer 4 | 0.5 | 0.03° C./min | 200° C./72 hours | 0 | 0 | 1.54 |
| Sample 8 | Polymer 5 | 0.5 | 0.03° C./min | 100° C./10 min | 22.5 | 14.3 | 3.26 |
| Sample 9 | Polymer 6 | 0.5 | 0.03° C./min | 60° C./10 hours | 15.3 | 4.1 | 0.46 |
| *Sample 10 | — | — | — | — | 15 | 10.5 | >100 |

*Not an example of the present invention.

Example 2

Multiple, substantially similar foam samples were prepared as follows. About 10 grams of Polymer 1 (carboxymethylcellulose) was dissolved in about 2000 grams of distilled water at a temperature of about 23° C. About 0.2 gram of citric acid was also added to the solution as a crosslinking agent. The solution was blended for about 2 to 3 hours to ensure thorough mixing of the components. About 500 grams of the solution was placed into a stainless steel pan, wherein the pan had dimensions of 10 inches (width) by 20 inches (length) by 1 inch (depth). The pan, containing the solution, was then placed in freeze dryer, available from The VirTis, Inc. of Gardiner, N.Y., under the designation VirTis Genesis model 25EL freeze dryer. The solution in the pan was then cooled down to about −15° C. at a cooling rate of about 0.04° C./minute in order to freeze the water in the solution. The solution in the pan were maintained at about −15° C. for about an hour to ensure substantially complete freezing of the water. The frozen solutions were left in the freeze dryer and then subjected to a vacuum of about 105 millitorrs, provided by a vacuum pump which had a condenser set to a temperature of about −60° C. to about −70° C., for about 15 hours.

The resultant foam structures were then treated at various temperatures for various periods of time in order to assist in the crosslinking of the polymers. The final foam structures were then evaluated for Free Swell, Absorbency Under Load, and Softness values. The various process conditions and results of the evaluations for the various samples are summarized in Table 2.

TABLE 2

| Sample No. | Heat Treatment Conditions (Temperature/ Time) | Free Swell Value (g/g) | Absorbency Under Load Value (g/g) | Softness Value (g/gsm) |
|---|---|---|---|---|
| *Sample 11 | None | 0 | 0 | 20.58 |
| Sample 12 | 150° C./5 min | 27.9 | — | — |
| Sample 13 | 150° C./10 min | 25.1 | 14.3 | — |
| Sample 14 | 150° C./20 min | 15.7 | 11.2 | — |
| Sample 15 | 150° C./30 min | 16.6 | 11.3 | 20.58 |
| *Sample 16 | None | 0 | 0 | — |
| Sample 17 | 130° C./5 min | 60.1 | 29.9 | 20.58 |
| Sample 18 | 130° C./10 min | 26.1 | 18.3 | — |
| Sample 19 | 130° C./15 min | 21.8 | 16.2 | — |
| Sample 20 | 130° C./20 min | 18.2 | 14.6 | — |
| Sample 21 | 130° C./25 min | 17.4 | 13.9 | 20.58 |

*Not an example of the present invention.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A process for preparing an absorbent foam wherein the absorbent foam comprises a water-swellable, water-insoluble polymer, the process comprising:

a. forming a solution comprising a weight amount of water and a polymer, wherein the polymer is present in the solution in a weight amount between about 0.1 to about 30 weight percent, based on total solution weight;

b. cooling the solution to a temperature between about −50° C. and about 0° C. at a cooling rate that is less than about 0.4° C. per minute under conditions effective to freeze the water;

c. substantially removing the frozen water from the solution; and d. recovering a polymeric foam.

2. The process of claim 1 wherein the frozen water is removed from the solution by use of a vacuum of less than about 500 millitorrs.

3. The process of claim 2 wherein less than about 20 weight percent of the weight amount of water in the solution remains in the recovered absorbent foam.

4. The process of claim 1 wherein the process further comprises treating the polymeric foam under conditions effective to achieve a water-swellable, water-insoluble polymer.

5. The process of claim 4 wherein the polymeric foam is treated with a treatment selected from the group consisting of heat treatment, exposure to ultraviolet light, exposure to microwaves, exposure to an electron beam, steam treatment, high humidity treatment, high pressure treatment, and treatment with an organic solvent.

6. The process of claim 5 wherein the polymeric foam is treated with a temperature between about 50° C. to about 250° C.

7. The process of claim 1 wherein the solution further comprises a crosslinking agent.

8. The process of claim 7 wherein the crosslinking agent is selected from the group consisting of an organic compound having at least two functional groups or functionalities capable of reacting with the polymer and a metal ion with two or more positive charges.

9. The process of claim 1 wherein the polymer is a water-soluble polymer.

10. The process of claim 1 wherein the polymer is selected from the group consisting of polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyacrylamides, polyquaternary ammoniums, carboxymethyl celluloses, carboxymethyl starchs, hydroxypropyl celluloses, algins, alginates, carrageenans, acrylic grafted starchs, acrylic grafted celluloses, chitin, chitosan, polyaspartic acid, polyglutamic acid, polyasparagins, polyglutamines, polylysines, polyarginines, and the salts, copolymers, and mixtures of any of the foregoing polymers.

11. The process of claim 10 wherein the polymer is selected from the group consisting of polyacrylic acids, carboxymethyl celluloses, chitin, chitosan, and the salts, copolymers, and mixtures of any of the foregoing polymers.

12. The process of claim 1 wherein the water-swellable, water-insoluble polymer is present in the absorbent foam in a weight amount between about 50 weight percent to 100 weight percent, based on the total weight of the absorbent foam.

13. The process of claim 1 wherein the absorbent foam exhibits a Free Swell value of at least about 10 grams of liquid per gram of absorbent foam and a Softness value that is less than about 30 grams of force per gram per square meter of the absorbent foam.

14. The process of claim 13 wherein the absorbent foam comprises cells comprising walls having a thickness wherein the average cell size of the cells is between about 10 microns to about 100 microns, and wherein the average wall thickness of the cells is between about 0.1 micron to about 30 microns.

15. The process of claim 1 wherein the absorbent foam comprises cells comprising walls having a thickness wherein the average cell size of the cells is between about 10 microns to about 100 microns, and wherein the average wall thickness of the cells is between about 0.1 micron to about 30 microns.

16. The process of claim 1 wherein the polymer is selected from the group consisting of polyacrylic acids, carboxymethyl celluloses, chitin, chitosan, and the salts, copolymers, and mixtures of any of the foregoing polymers; the solution further comprises a crosslinking agent; the frozen water is removed from the solution by use of a vacuum of less than about 500 millitorrs and less than about 20 weight percent of the weight amount of water in the solution remains in the recovered absorbent foam; the process further comprises treating the polymeric foam with a treatment selected from the group consisting of heat treatment, exposure to ultraviolet light, exposure to microwaves, exposure to an electron beam, steam treatment, high humidity treatment, high pressure treatment, and treatment with an organic solvent; the water-swellable, water-insoluble polymer is present in the absorbent foam in a weight amount between about 50 weight percent to 100 weight percent, based on the total weight of the absorbent foam; the absorbent foam exhibits a Free Swell value of at least about 10 grams of liquid per gram of absorbent foam, an Absorbency Under Load value of at least about 10 grams of liquid per gram of absorbent foam, and a Softness value that is less than about 30 grams of force per gram per square meter of the absorbent foam; and the absorbent foam comprises cells comprising walls having a thickness wherein the average cell size of the cells is between about 10 microns to about 100 microns and the average wall thickness of the cells is between about 0.1 micron to about 30 microns.

17. An absorbent foam prepared by the process of claim 1.

18. The absorbent foam of claim 17 wherein the polymer is selected from the group consisting of polyacrylic acids, carboxymethyl celluloses, chitin, chitosan, and the salts, copolymers, and mixtures of any of the foregoing polymers; the water-swellable, water-insoluble polymer is present in the absorbent foam in a weight amount between about 50 weight percent to 100 weight percent, based on the total weight of the absorbent foam; the absorbent foam exhibits a Free Swell value of at least about 10 grams of liquid per gram of absorbent foam, an Absorbency Under Load value of at least about 10 grams of liquid per gram of absorbent foam, and a Softness value that is less than about 30 grams of force per gram per square meter of the absorbent foam; and the absorbent foam comprises cells comprising walls having a thickness wherein the average cell size of the cells is between about 10 microns to about 100 microns and the average wall thickness of the cells is between about 0.1 micron to about 30 microns.

* * * * *